(12) United States Patent
Crandall et al.

(10) Patent No.: US 6,309,391 B1
(45) Date of Patent: Oct. 30, 2001

(54) MULTIDIRECTIONAL PIVOTING BONE SCREW AND FIXATION SYSTEM

(75) Inventors: Dennis Crandall, Mesa, AZ (US); Matthew M. Morrison; Terrance Strohkirch, both of Cordova, TN (US)

(73) Assignee: SDGI Holding, Inc., Wilmington, DE (US)

( * ) Notice: Subject to any disclaimer, the term of this patent is extended or adjusted under 35 U.S.C. 154(b) by 0 days.

(21) Appl. No.: 09/526,435

(22) Filed: Mar. 15, 2000

(51) Int. Cl.[7] ....................................................... A61B 17/56
(52) U.S. Cl. ................................................. 606/61; 606/73
(58) Field of Search ............................... 606/61, 72, 73

(56) References Cited

U.S. PATENT DOCUMENTS

| | | | |
|---|---|---|---|
| 5,002,542 | 3/1991 | Frigg | 606/61 |
| 5,196,013 | 3/1993 | Harms et al. | 606/61 |
| 5,486,174 | * 1/1996 | Fournet-Fayard et al. | 606/61 |
| 5,545,166 | 8/1996 | Howland | 606/61 |
| 5,569,247 | 10/1996 | Morrison | 606/61 |
| 5,591,166 | 1/1997 | Bernhardt et al. | 606/61 |
| 5,628,740 | 5/1997 | Mullane | 606/61 |
| 5,643,263 | 7/1997 | Simonson | 606/61 |
| 5,649,926 | 7/1997 | Howland | 606/61 |
| 5,725,528 | * 3/1998 | Errico et al. | 606/61 |
| 5,743,907 | * 4/1998 | Asher et al. | 606/61 |
| 5,752,957 | 5/1998 | Ralph et al. | 606/61 |
| 5,766,254 | 6/1998 | Gelbard | 623/17 |
| 5,800,435 | 9/1998 | Errico et al. | 606/61 |
| 5,810,819 | 9/1998 | Errico et al. | 606/61 |
| 5,885,285 | 3/1999 | Simonson | 606/61 |
| 5,938,663 | 8/1999 | Petreto | 606/61 |
| 5,947,966 | * 9/1999 | Drewry et al. | 606/61 |
| 5,976,135 | 11/1999 | Sherman et al. | 606/61 |
| 5,980,521 | 11/1999 | Montague et al. | 606/61 |
| 5,989,250 | 11/1999 | Wagner et al. | 606/61 |
| 6,017,344 | 1/2000 | Errico et al. | 606/61 |
| 6,146,383 | * 11/2000 | Studer et al. | 606/61 |
| 6,187,005 | 2/2001 | Brace et al. | 606/61 |

* cited by examiner

Primary Examiner—Paul J. Hirsch
Assistant Examiner—Melba Bumgarner
(74) Attorney, Agent, or Firm—Woodard, Emhardt, Naughton Moriarty & McNett (57) ABSTRACT

A double-jointed bone bolt for use in an apparatus for maintaining vertebra in a desired relationship. The apparatus has a rod that extends substantially along the spine and one or more bone bolts. At least one of the bone bolts is double jointed. The double-jointed bolt has a mounting portion with a hook or coarse threads to engage a vertebra, and the mounting portion is attached to a pivot post in a manner that allows the pivot post to be rotatable about a common axis in respect to the mounting portion. The pivot post of the bone bolt is then pivotally attached to a connector portion of the bone bolt that has machine threads upon which a surgeon may attach a clamp. The clamp has a second bolt and an arm. The second bolt holds the rod and the arm to the clamp. The second bolt has a first channel to attach to the rod, while the arm has a second channel to attach the double-jointed bone bolt.

21 Claims, 11 Drawing Sheets

MULTIDIRECTIONAL PIVOTING BONE SCREW AND FIXATION SYSTEM

This invention relates to orthopedics and spinal surgery, and more particularly relates to a double-hinged bone screw to accommodate the differences in position of adjacent bolts implanted in adjacent vertebrae, which bolts are all mounted to a common spinal rod.

BACKGROUND

Spinal implant systems provide a rod for supporting the spine and properly positioning components of the spine for various treatment purposes. Bolts or screws are typically secured into the vertebrae for connection to a supporting rod. These bolts must frequently be positioned at various angles due to the anatomical structure of the patient, the physiological problem to be treated, and the preference of the physician. It is difficult to provide secure connection between the spinal support rod and these connecting bolts at various angles, and where there are differing distances between the rod and bolts and different heights relative to these components.

SUMMARY OF THE INVENTION

In one aspect, this invention is a bolt for connecting a vertebra to a longitudinal member. The bolt has a mounting portion with a hook or coarse threads to engage a vertebra. The mounting portion is attached to a pivot post in a manner that allows the pivot post to be rotatable about a common axis in respect to the mounting portion of the bolt. The pivot post is then pivotally attached to a connector portion that has machine threads upon which a surgeon may attach other structures.

In another aspect, this invention is an apparatus for maintaining vertebra in a desired relationship. The apparatus has a rod that extends substantially along the spine and one or more bone bolts. At least one of the bone bolt has a mounting portion with a hook or coarse threads to engage a vertebra, and the mounting portion is attached to a pivot post in a manner that allows the pivot post to be rotatable about a common axis in respect to the mounting portion of the bolt. The pivot post of the bone bolt is then pivotally attached to a connector portion of the bone bolt that has machine threads upon which a surgeon attaches a clamp. The clamp, also a part of this embodiment of the invention, has a second bolt and an arm. The second bolt holds the rod and the arm to the clamp. The second bolt has a first channel to hold the rod while the arm has a second channel to hold the bone bolt.

It is an object of this invention to provide a connection assembly that will allow connection between a spinal support rod to a vertebra at a variety of angles relative to the vertical, taken when the patient is lying down.

DESCRIPTION OF THE PREFERRED EMBODIMENT

Specific language is used in the following description to publicly disclose the invention and to convey its principles to others. No limits on the breadth of the patent rights based simply on using specific language are intended. Also included are any alterations and modifications to the description that should normally occur to one of average skill in this technology.

Figure 1:
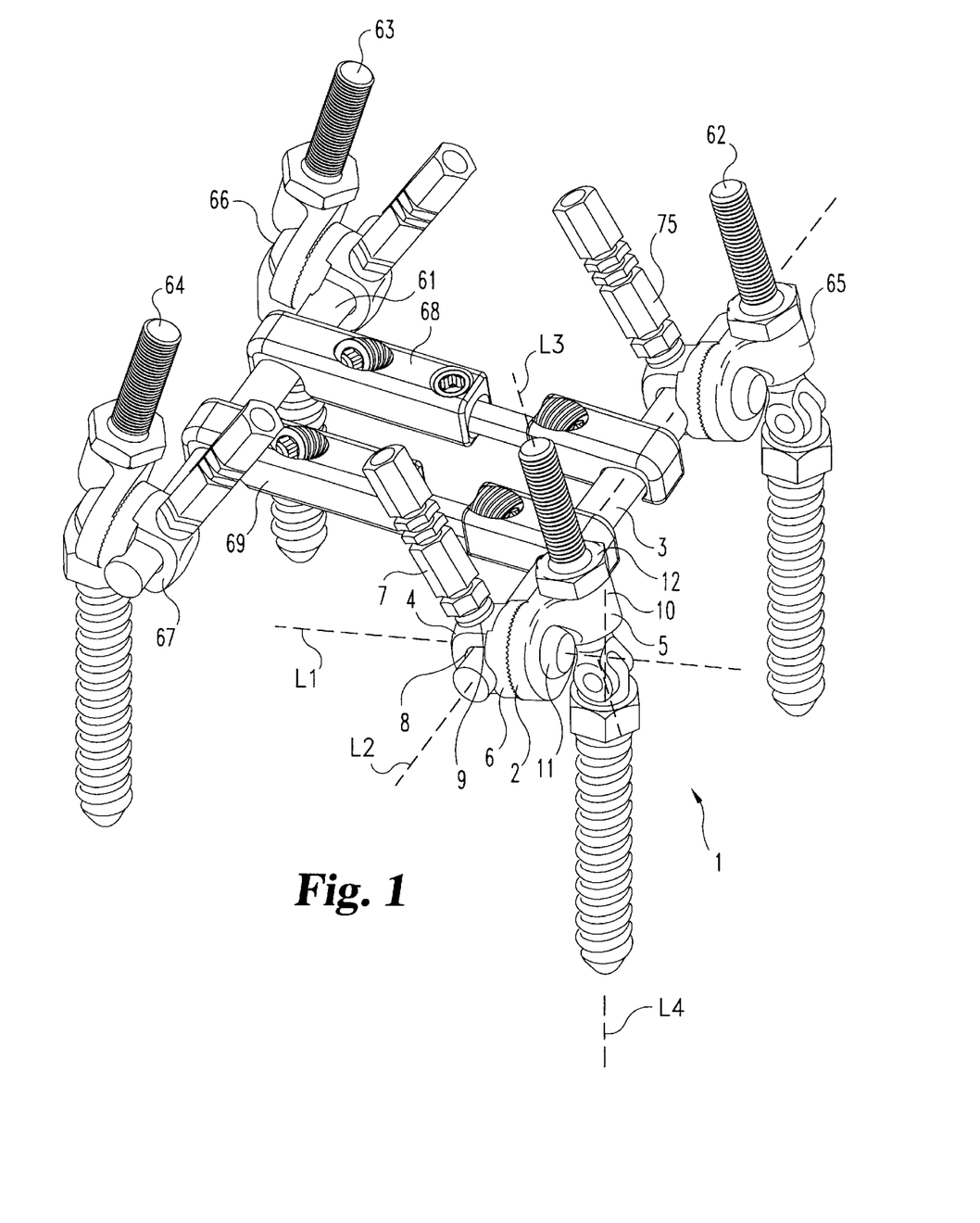
FIG. 1 is a perspective view of one embodiment of the present invention.

A bone bolt 1 according to one embodiment of the invention is shown as part of a larger spinal implant system in FIG. 1. Bone bolt 1 is shown attached to a clamp 2 with the longitudinal axis L1, and clamp 2 is shown attached to a spinal implant rod 3 with a longitudinal axis L2. Clamp 2 includes a clamp bolt 4, an arm 5, a rod interface washer 6, a set screw 7, and a nut 12. Clamp bolt 4 has an aperture 8 for receiving rod 3, and while the aperture is shown closed around rod 3, it will nevertheless be understood that an open-sided aperture may also be used to permit top-loading of rod 3 into clamp 2. Set screw 7 is inserted through a threaded opening 9 and into aperture 8 in clamp bolt 4 so as to allow set screw 7 to push against rod 3. Arm 5 has a bore 10 for receiving bone bolt 1. Arm 5 is simultaneously tightened to clamp 2 when set screw 7 is tightened against rod 3. As set screw 7 pushes against rod 3, rod 3 pushes against rod interface washer 6, which pinches arm 5 between rod interface washer 6 and stop 11. In this manner, set screw 7 acts as a compression member to tighten clamp 2 and achieve substantial fixation of arm 5 to rod 3.

Figure 9:
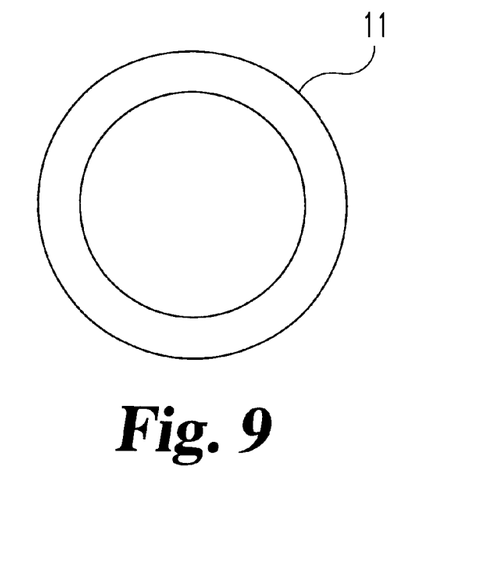
FIGS. 9–10 are respectively end and side views of a stop that may be used in one embodiment of the present invention.
Figure 10:
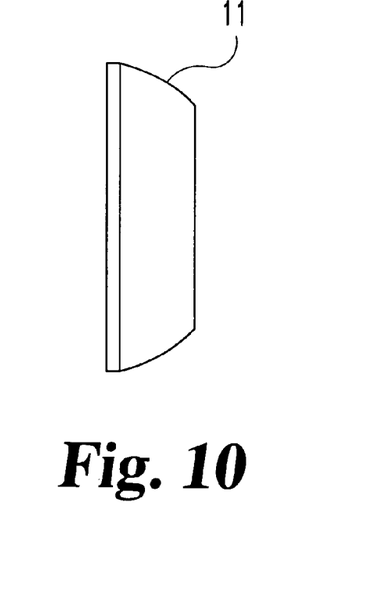
Figure 11:
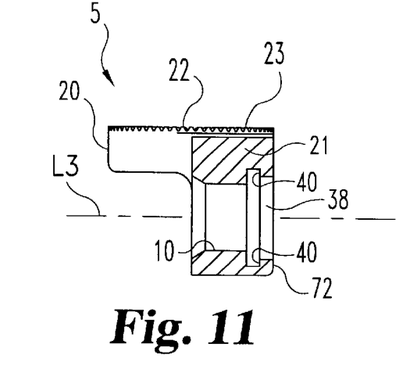
FIGS. 11–14 are respectively end cross-sectional, top, side, and side cross-sectional views of an arm that may be used in one embodiment of the present invention.

Details of clamp bolt 4 are shown in FIGS. 2–8. Clamp bolt 4 can be subdivided into bolt head portion 13, bolt shaft portion 14, washer seat portion 15 and washer stop portion 16. Threaded openings 9a & 9b, and aperture 8 reside in bolt head portion 13. Threaded openings 9a & 9b open into aperture 8 at an oblique angle A4 with respect to longitudinal axis L1 to allow set screw 7 (FIG. 1) to force spinal rod 3 toward the distal end 17 of aperture 8. Clamp bolt 4 is substantially symmetrical about longitudinal axis L1 such that threaded openings 9a and 9b are substantially mirror images. Bolt shaft portion 14 is generally cylindrical in shape and is sized to accept the eye 18 (FIGS. 13 & 14) of arm 5. Arm 5 is then held on shaft portion 14 by attaching stop 11 (shown in isolation in FIGS. 9 & 10) to the end 19 of shaft portion 14, either by welding or some other suitable means. As an alternative, shaft portion 14 may include threads and stop 11 may be correspondingly threaded onto shaft portion 14 to hold arm 5 in position. In this alternative design, stop 11 may be the compressive member utilized to tighten clamp 2 onto rod 3 instead a set screw threaded into bolt head portion 13.

Clamp bolt 4 also preferably includes washer seat portion 15 and washer stop portion 16. A washer seat portion 15 that is substantially rectangular in cross-section is currently preferred, but washer seat portion 15 can be of any suitable shape that may interlock with a complementary shape in rod interface washer 6 (FIGS. 1, 15, 16 & 17) to prevent rod interface washer 6 from rotating in relation to clamp bolt 4. As shown, a washer stop 16 is generally provided in clamp bolt 2 by placing a raised edge in bolt head portion 13. Washer stop 16 prevents rod interface washer 6 from being inadvertently removed from clamp 2.

Details of arm 5 are shown in FIGS. 11–14. Arm 5 includes a flange portion 20, and a collar portion 21. Flange portion 20 has an eye 18, and as previously presented, clamp bolt 4 attaches to arm 5 by placing the shaft portion 14 of clamp bolt 4 through eye 18 and then attaching stop 11 on end 19 of shaft portion 14. The medial face 22 of flange portion 20 also includes a connection surface 23. Connection surface 23 preferably includes structure for facilitating the engagement of arm 5 against rotational movement relative to rod interface washer 6. This engagement structure is preferably a plurality of variable angle ridges that radiate from the rotational center of eye 18. In other words, the structure is a set of interlocking teeth that can generally be characterized as male protrusions and complementary female cavities that upon interlock, prevent rod interface washer 6 from rotating in respect to arm 5.

Figure 12:
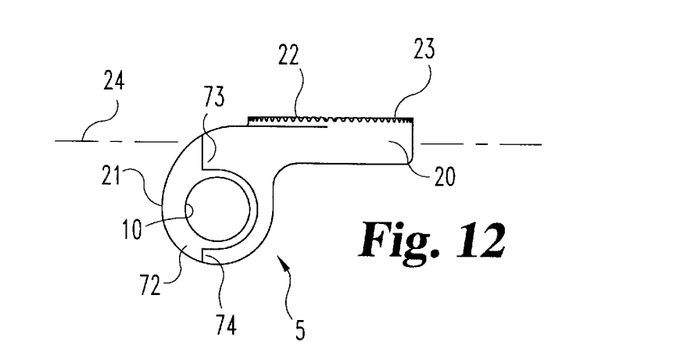
Figure 18:
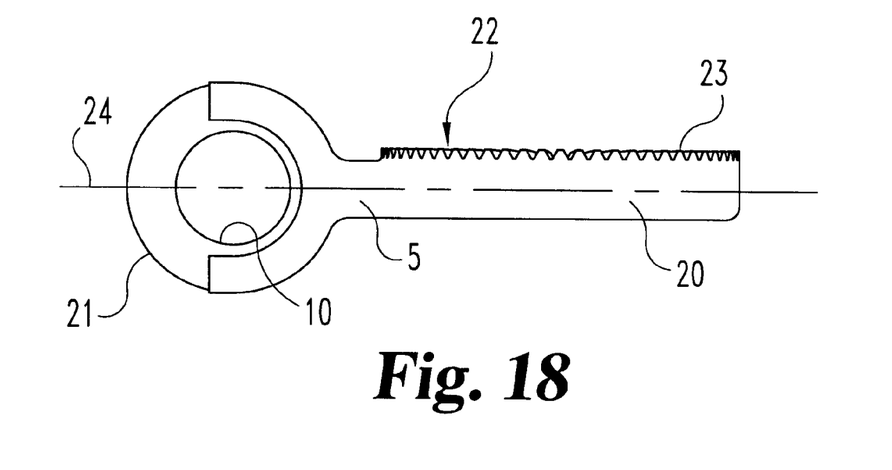
FIGS. 18, 19 are top views of alternative embodiments for an arm in the practice of the present invention.
Figure 19:
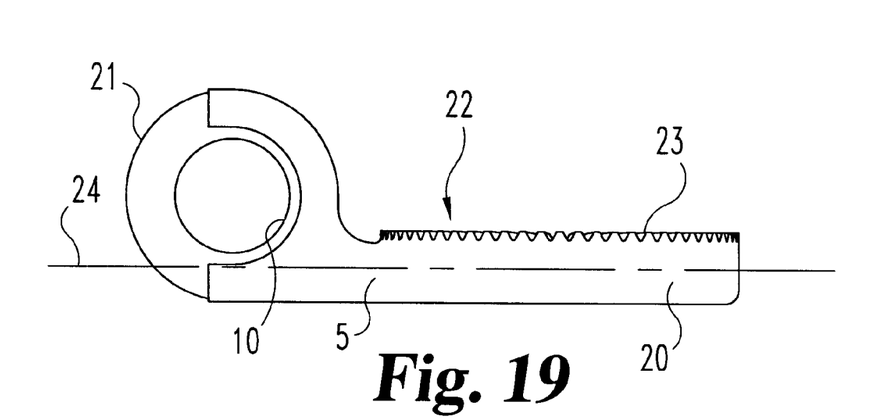

Referring to FIGS. 12, 18 and 19; collar portion 21 of arm 5 has a bore 10. Bore 10 may assume various orientations in relation to the centerline 24 of arm 5. FIG. 12 depicts bore 10 offset from centerline 24 toward the stop (not shown) of clamp bolt 4. Optionally, bore 10 can be offset from centerline 24 toward the clamp aperture 8 (not shown) of clamp bolt 4, as shown in FIG. 19, or bore 10 can be placed in the same plane as centerline 24, as shown in FIG. 18. It being understood that the alternative arm designs may permit even a smaller total width of clamp 2 by bringing bone bolt 1 closer to the rod 3.

Figure 20:
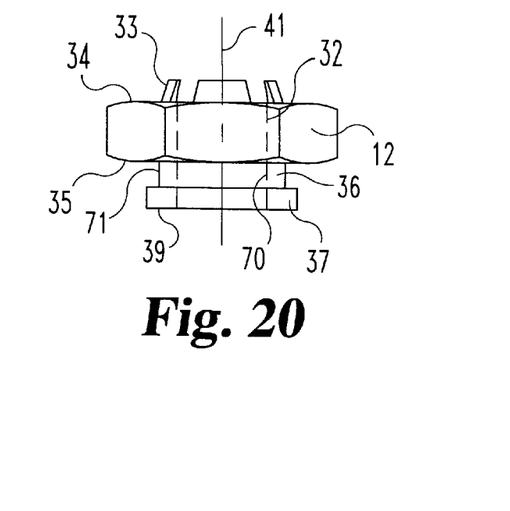
FIG. 20 is a side view of a nut that may be used in one embodiment of the present invention.

Referring to FIG. 20, there is shown nut 12, which is preferably used to threadably engage bone bolt 1 (not shown) to arm 5, and prevent bone bolt 1 from moving longitudinally along longitudinal axis L3 with respect to arm 5. Nut 12 has as set of internal threads 32 to mate with the machine threads 60 on bone bolt 1 and a set of locking tabs 33 on the proximal face 34 of nut 12 to firmly hold nut 12 upon bone bolt 1 once nut 12 is threaded into place. The distal face 35 of nut 12 also includes an annular collar 36. Annular collar 36 is integrally connected to nut 12, and has a channel 70 that opens into internal threads 32. The end 39 of collar 36 terminates in an annular rim 37 that laterally projects beyond the diameter of annular collar 36, and forms an annular groove 71 between annular rim 37 and distal face 35 of nut 12.

Referring back to FIGS. 11–14, arm 5 is preferably adapted to rotatably secure nut 12 by annular rim 37 and annular collar 36. The proximal face 72 of collar portion 21 of arm 5 includes a semicircular cavity 38 around the entrance of bore 10 that is sized to accept annular collar 36 and annular rim 37. By fitting collar 36 and rim 37 into cavity 38, annular rim 37 rides against semi-circular lip 40, on the roof of cavity 38; opening 70 and internal threads 32 of nut 12 are axially aligned with bore 10 of arm 5; and nut 12 is rotatably secured to arm 5. In other words, nut 12 is free to rotate about axis 41 or axis L3, but nut 12 is substantially fixed against movement along longitudinal axis L3 (FIGS. 11 & 13) relative to arm 5 because annular rim 37 rides against semi-circular lip 40 in one direction and proximal face 72 in the other. In one preferred embodiment, nut 12 is temporarily held in semicircular cavity 38 by slightly bending corners 73 & 74 of lip 40 against annular rim 37. Bending these corners will temporarily hold nut 12 in arm 5 until the surgeon threads nut 12 onto bone bolt 1, and will not significantly hinder the surgeon's rotation of nut 12 around bone bolt 1.

Figure 15:
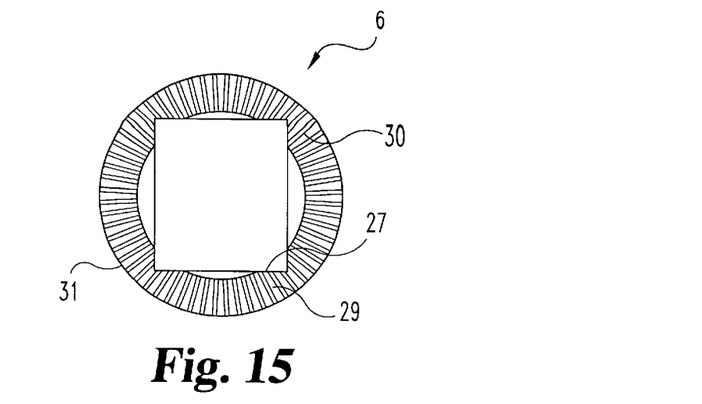
FIGS. 15–17 are respectively end, side, and top views of a washer that may be used in one embodiment of the present invention.
Figure 16:
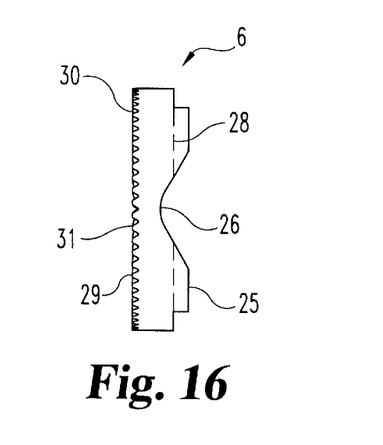
Figure 17:
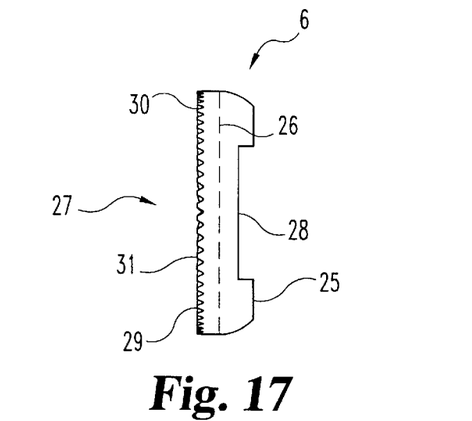

Details of rod interface washer 6 are shown in FIGS. 15, 16 & 17. Rod interface washer 6 can be any of several suitable shapes, including the circle that is depicted. The medial face 25 of the rod interface washer 6 has an engagement surface, which preferably includes an engagement groove 26 that accepts a cylindrical spinal implant rod (such as rod 3 in FIG. 1). Engagement groove 26 preferably runs across the entire face of medial face 25. Rod interface washer 6 also has a central opening 27 that corresponds to the cross-sectional shape of previously presented washer seat portion 15 in clamp bolt 4. In the currently preferred embodiment, both washer seat portion 15 and opening 27 are substantially square. Although, this shape could vary from many possible shapes that would similarly prevent rod interface washer 6 from rotating in respect to clamp bolt 4. To assist in this regard, it is also preferable that rod interface washer have a guide groove 28 to accept bolt head portion 13 of clamp bolt 4 to further lock clamp bolt 4 and rod interface washer 6 together. It should be noted that guide groove 28 and engagement groove 26 are preferably placed in such a manner that orients aperture 8 substantially parallel to groove 26. This placement helps insure that spinal rod 3 will be held in the connector assembly in a direction that is substantially perpendicular to clamp bolt 4, and in turn, also substantially perpendicular to set screw 7.

Figure 13:
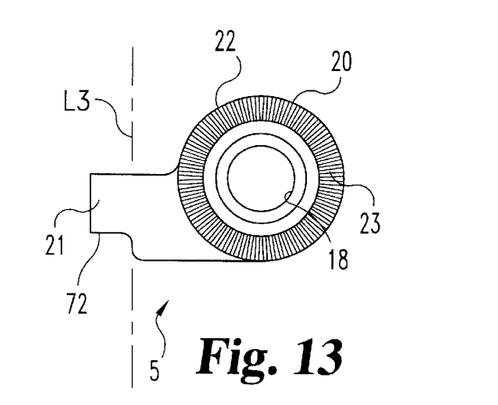
Figure 14:
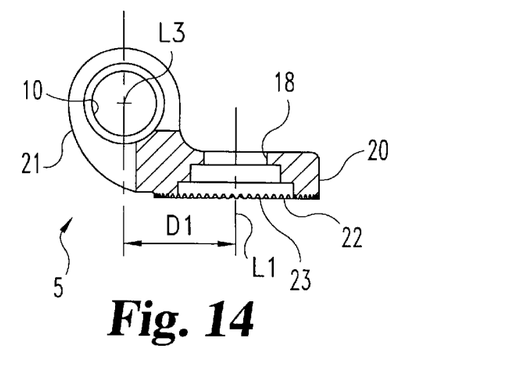

Rod interface washer 4 also includes connection surface 29 on the lateral face 30 of rod interface washer 6. Connection surface 29 preferably includes structure for facilitating the engagement of rod interface washer 6 against rotational movement relative to arm 5. This engagement structure is preferably a plurality of variable angle ridges 31 that radiate from the rotational center of rod engagement washer 6, similar to those previously described on the medial face 22 on flange 20 of arm 5. Variable angle ridges 31 are sized to mate with the similar variable angle ridges 23 on arm 5. Referring to FIGS. 13 and 15, both sets of ridges consist of alternating male protrusions and female cavities. Hence, once placed together, these interlocking ridges prevent rod engagement washer 6 from rotating in respect to arm 5. And although radiating ridges are shown to facilitate the fixation of these two parts, it is also contemplated that other structures could serve this function. For example, it is also contemplated that one could use any number of interlocking male and female structures such as rounded bumps or knurling and mating cavities. The locking engagement of connection surface 23 with connection surface 29 may occur at any of a plurality of angles. More specifically, the angle between longitudinal axis L3 of bone bolt 1 and the longitudinal axis L2 of rod 3 may be adjusted to meet the requirements of the patient's anatomy.

Figure 25:
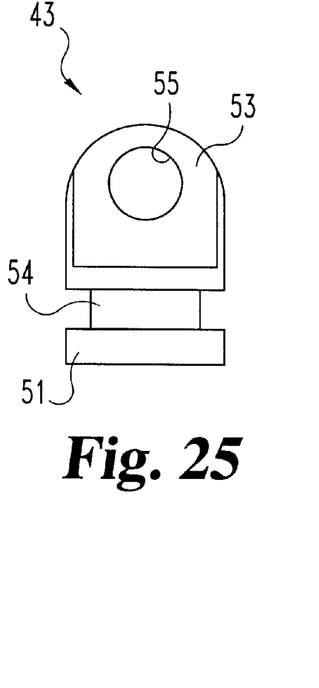
FIGS. 25 and 26 are respectively front and side view of a pivot post in a bone bolt according to one embodiment of the present invention.
Figure 26:
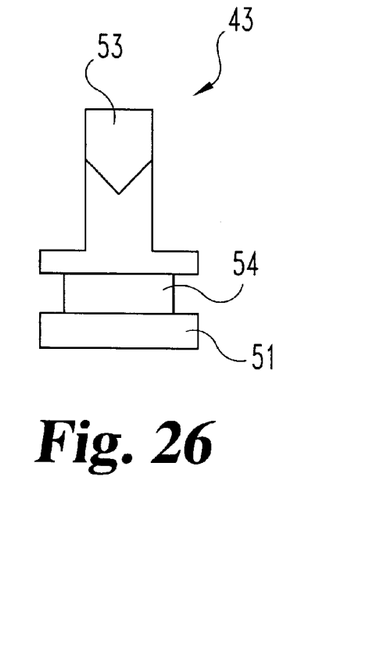
Figure 27:
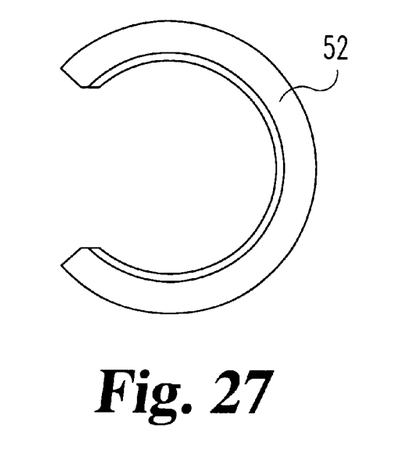
FIG. 27 is a top view of a snap ring for a bone bolt according to one embodiment of the present invention.

Details of bone bolt 1 can be seen in FIGS. 21–28. Bone bolt 1 includes a mounting portion 42, a pivot post 43, and a connector portion 44. The distal end of mounting portion 21 has a set of coarse threads 45. Coarse threads 45 have a thread convolution for engaging cancellous bone and terminate in a tapered tip 46. Tapered tip 46 helps align bone bolt 1 into a predrilled opening in a vertebra and also helps coarse threads 45 to gradually engage and advance into the vertebra upon rotation of mounting portion 21. In this regard, although coarse threads are shown as a means for engaging a vertebra, it is also contemplated that a hook, mounted on the end of mounting portion 42, could also be used as an alternative means to engage a vertebra. The proximal end 47 of mounting portion 42 terminates in hex-headed drive portion 49. The inside of hex-headed drive portion 49 includes an annular receptacle 48, and the inner wall of receptacle 48 has an annular groove 50. (FIG. 22) Annular receptacle 48 is sized to accept hub 51 of pivot post 43 (FIGS. 25 & 26), and annular groove 50 is sized to accept snap ring 52. (FIG. 27)

Pivot post 43 is shown in isolation in FIGS. 25 & 26. Pivot post 43 has a hub 51 and an ear 53 with a channel 55. Hub 51 preferably has a circular cross-section and is circumscribed by an annular groove 54. Hub 51 is sized to freely rotate about longitudinal axis L4 inside receptacle 48 of the mounting portion 42 of bone bolt 1. During assembly in one preferred embodiment, snap ring 52 (FIG. 27) is placed partly inside annular groove 54 before hub 51 is inserted into receptacle 48. Then, upon insertion into receptacle 48, snap ring 52 partially expands into annular groove 50, and thereby rotatably connects pivot post 53 to the proximal end 47 of mounting portion 42.

Figure 21:
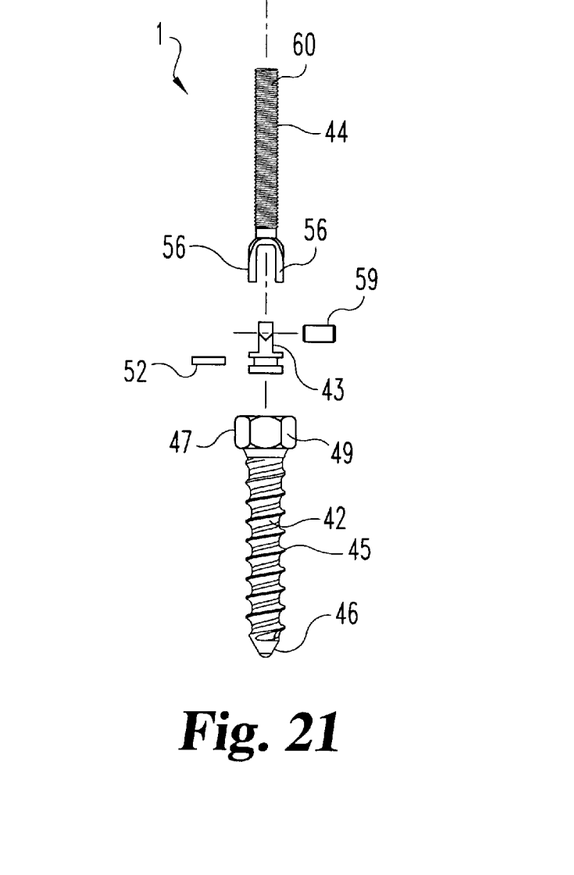
FIG. 21 is an exploded view of a bone bolt in one embodiment of the present invention.
Figure 22:
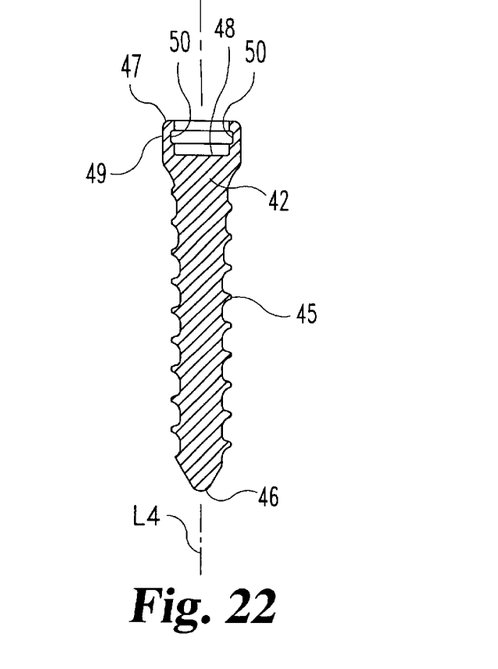
FIG. 22 is a cross-sectional view of a mounting portion of a bone bolt according to one embodiment of the present invention.
Figure 23:
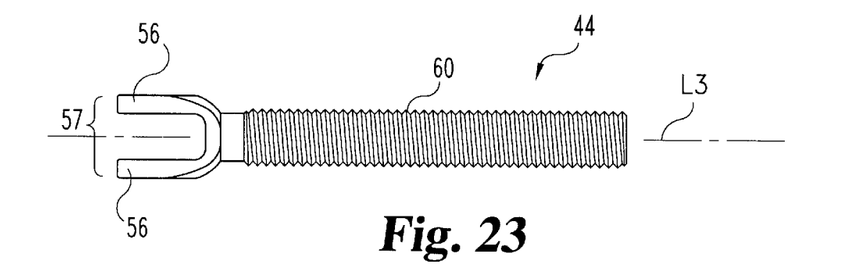
FIGS. 23 and 24 are respectively side and top views of a connecting portion of a bone bolt according to one embodiment of the present invention.
Figure 24:
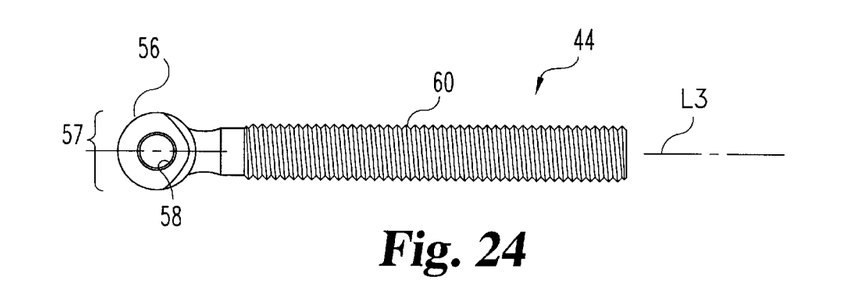
Figure 28:
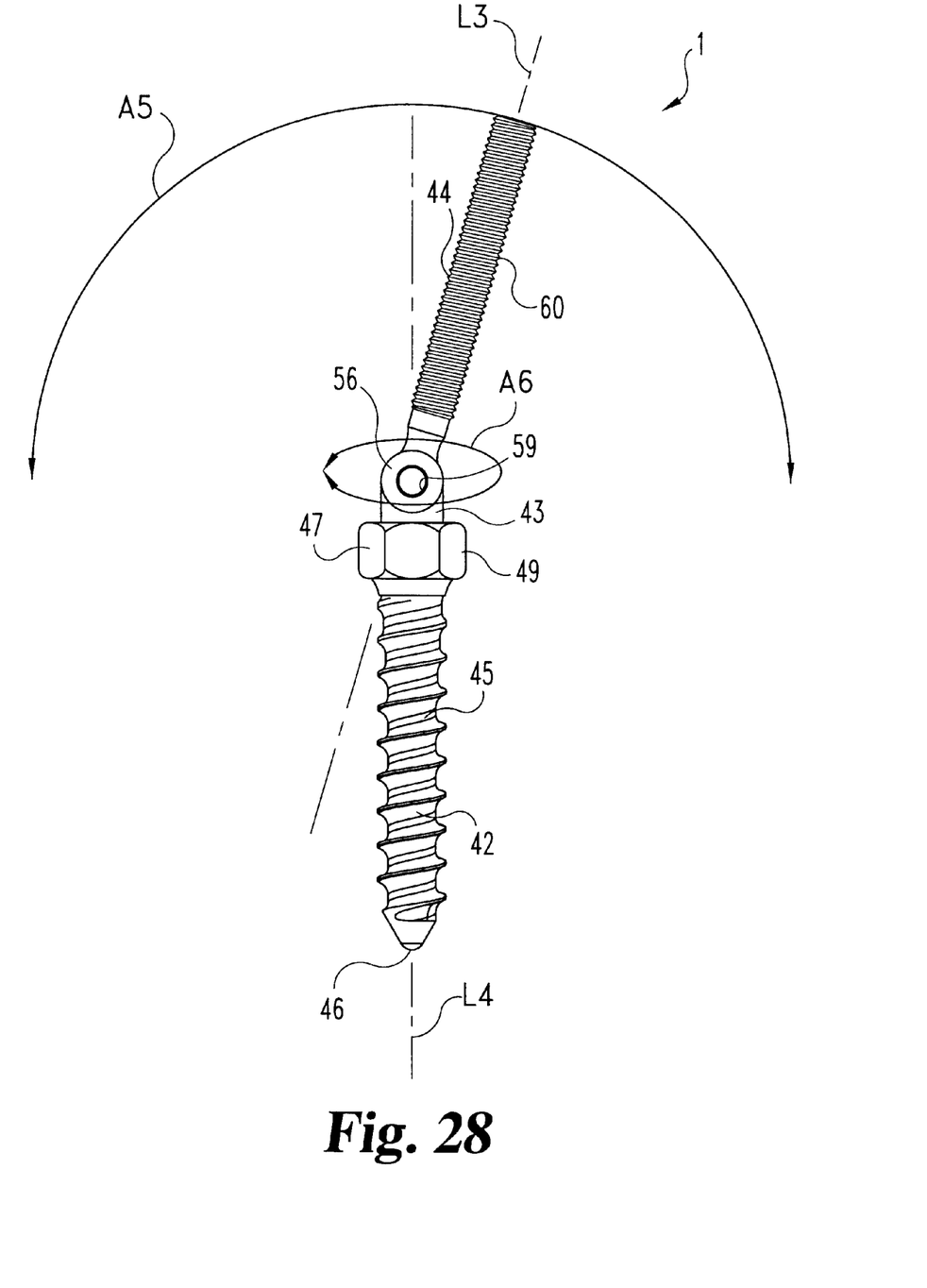
FIG. 28 is a side view of a bone bolt according to one embodiment of the present invention.

A top and side view of the connector portion 44 of bone bolt 1 is shown in FIGS. 23 & 24. Most of the longitudinal length of connector portion 44 is circumscribed with machine threads 60. The lower end 57 of connector portion 44 terminates with a pair of ears 56 that are diametrically opposite of each other at the radial perimeter of end 57. Each of the ears 56 includes an aperture or channel 58 for insertion of pin 59 (FIG. 21). During assembly, pin 59 is inserted through aperture 58 in one ear, then through channel 55 in pivot post 43, and then through aperture 58 in the other ear. Thusly joined to mounting portion 42 and pivot post 43, the connector portion 44 of bolt 1 may be pivoted around pin 59 as depicted by arc A5, and may also be rotated around longitudinal axis L4 of the mounting portion 42, as depicted by arc A6. (FIG. 28)

Referring back to FIG. 1, a typical construct in the use of this invention typically has two or more largely identical rods, 1 and 61, and at least two or more bone bolts 1, 62–64 attached to each rod by clamps 2, 65–67. And optionally, the rods may be joined by one or more cross-linking members 68 & 69. An example of a suitable cross-linking member is described in U.S. Pat. No. 5,947,966 to Drewry et al, the disclosure of which is specifically incorporated into this specification by reference. And although each of the clamps and bone bolts shown in this figure are identical, it is further contemplated that other clamps and bone bolts could be incorporated in a common construct in the use of this invention. For example, one could also use the clamps and bone bolts described in U.S. Pat. Nos. 5,643,263 and 5,885,285 to Simonson, the disclosures of which are specifically incorporated into this specification by reference with one or more of the bone bolts described herein.

Figure 2:
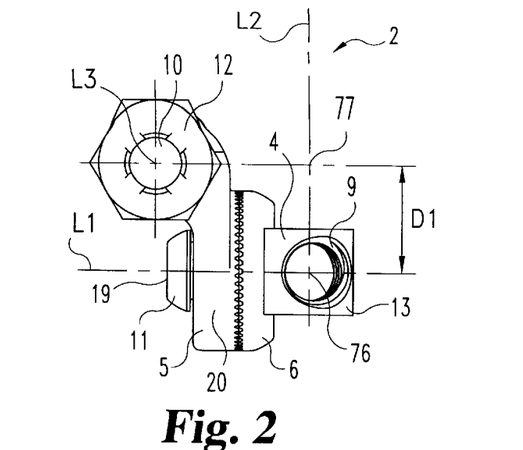
FIGS. 2–4 are respectively top, side, and cross-sectional views of a clamp that may be used in one embodiment of the present invention.
Figure 3:
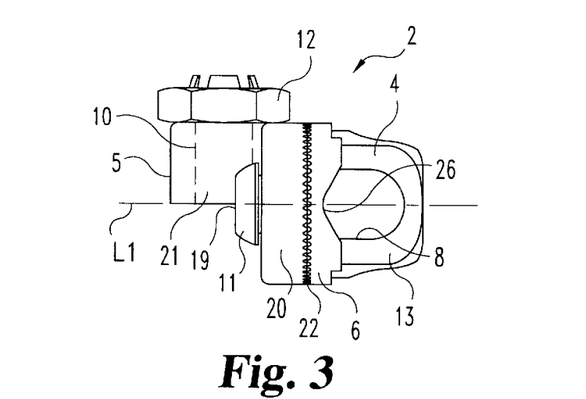
Figure 4:
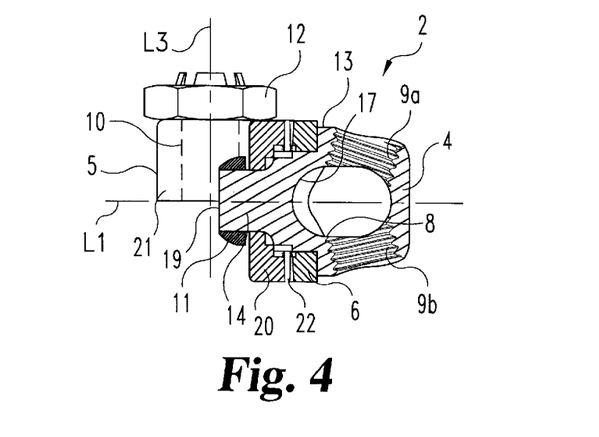
Figure 5:
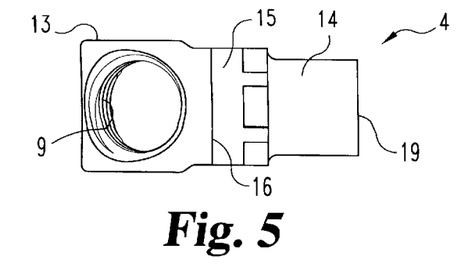
FIGS. 5–8 are respectively, top, side, end, and cross-sectional views of a clamp bolt that may be used in one embodiment of the present invention.
Figure 6:
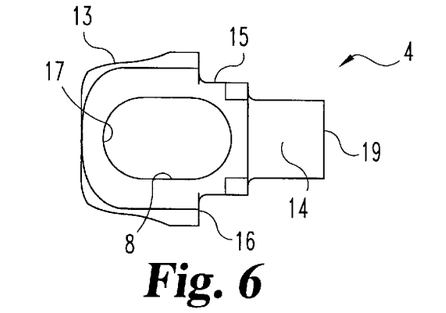
Figure 7:
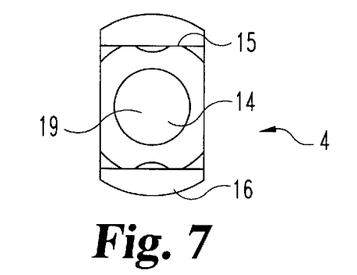
Figure 8:
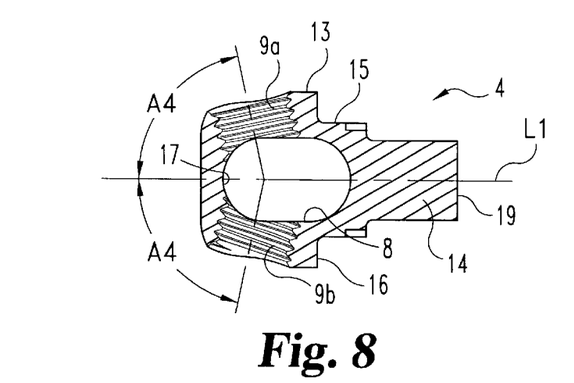

Clamp 2 is depicted in FIGS. 2–4, less set screw 7, which has been removed for clarity along with rod 3 and bone bolt 1. The clamp is used by placing spinal rod 3 through aperture 8. The connector portion 44 of bone bolt 1 is then threaded through bore 10 and nut 12 of clamp 2 as the surgeon desires. Arm 5 and the variable angle ridges 31 on the rod interface washer 6 are then interlocked with the variable angle ridges 23 on arm 5, and the assembly is tightened by threading set screw 7 into either of the threaded openings 9, (or by optionally turning stop 11 around connector portion 44 as described in an alternative embodiment). Upon entering aperture 8, set screw 7 contacts the spinal rod and forces the spinal rod toward interface washer 6. The spinal rod then contacts rod interface washer 6, and engages groove 26. As one continues turning set screw 7, rod interface washer 6 presses flange portion 20 of arm 5 against stop 11. The variable angle surfaces, item 23 on arm 5 and item 31 on rod interface washer 6, firmly engage each other and prevent rod interface washer 6 from rotating in relation to arm 5, which further locks arm 5 in relation to clamp bolt 4 because rod interface washer 6 cannot rotate in relation to clamp bolt 4. Adjustments can be made by loosening set screw 5 then re-tightening the set screw when the preferred position has been located. The surgeon can adjust the longitudinal position of bone bolt 1 by rotating nut 12 as the surgeon desires. The set screws 7 shown in FIG. 1 are of a type that shear at 75 when the appropriate amount of torque has been placed on set screw 7. Such set screws are now well-known in this art.

Referring to FIGS. 1 & 2, one may note some additional features of this invention by noting the locations of various longitudinal axes. L1 is the longitudinal axis of a portion of clamp 2. L2 is the longitudinal axis of rod 3, and L3 is the longitudinal axis of both connecter portion 44 of bolt 1 and bore 10 in arm 5. In this regard, one may not that L3 is offset from L1 a distance D1. In other words, clamp 2 will contact rod 3 at 76, and L3 or bore 10 spaced from 76 a distance D1 along rod 3. In many circumstances involving patient anatomy, distance D1 may help the surgeon place clamp 2 and/or bone bolt 1 in a manner that avoids interfering with the patient's anatomy, such as the facet joints of the spine.

While the invention has been illustrated and described in detail, this is to be considered as illustrated and not restrictive of the patent rights. The reader should understand that only the preferred embodiments have been presented and all changes and modifications that come with the sprit of the invention are included if the following claims or the legal equivalent of these claims describes them.

We claim:

1. A bolt for connecting a vertebra to a longitudinal member, comprising:

a mounting portion, said mounting portion having means for engaging a vertebra;

a pivot post, said mounting portion and said pivot post being, to one another so as to be rotatable about a connection axis;

a connector portion pivotally attached to said connector post, said pivot portion having machine threads.

2. The bolt of claim 1, including means for attaching a wrench to said mounting portion.

3. The bolt of claim 1, where said mounting portion has a proximal end and said pivot post has a distal end, and the proximal end of said mounting portion and the distal end of said post have mutually engageable male and female contacts, and wherein said contacts are adapted to allow said pivot post to rotate in respect to said mounting portion.

4. The bolt of claim 1, including a snap ring operably connecting said mounting portion and said post.

5. The bolt of claim 1, wherein said mounting portion has a length and said means for engaging are coarse threads disposed over at least a portion of the length of said mounting portion.

6. An assembly for maintaining vertebra in a desired relationship, comprising:

a rod having a first longitudinal axis extending substantially along the spine;

a bone bolt, said bone bolt including a mounting portion, a pivot post and connector portion, said mounting portion having means for engaging a vertebra; said mounting portion and said pivot post being engaged to one another so as to be rotatable about a connection axis; said connector portion pivotally attached to said pivot post, and said connector portion having machine threads and a second longitudinal axis; and a clamp, said clamp including a second bolt and an arm, said second bolt having a first channel for receiving a portion of the rod and a portion with a third longitudinal axis, said arm joined to said second bolt, said arm having a second channel for receiving the machine threads of said bone bolt.

7. The assembly of claim 6, wherein said second bolt engages said rod at a first longitudinal position and said bone bolt is spaced from said first longitudinal position along the first longitudinal axis.

8. The assembly of claim 6, wherein the second channel in said arm is offset from said third longitudinal axis along the first longitudinal axis.

9. The assembly of claim 6, including a nut rotatably threaded over the machine threads of said bone bolt and rotatably connected to the arm of said clamp.

10. The assembly of claim 6, wherein the second longitudinal axis of said connector portion of said bone bolt is offset from the third longitudinal axis of said portion of said clamp along the first longitudinal axis of said rod.

11. The assembly of claim 6, wherein said arm has a centerline and the second channel of said arm is laterally offset from the centerline toward said rod.

12. The assembly of claim 6, wherein said arm has a centerline and the second channel of said arm is laterally offset from the centerline away from said rod.

13. The assembly of claim 6, wherein said arm has a certerline and the second channel of said arm resides in the same plane as the centerline.

14. The assembly of claim 6, wherein said arm may be fixedly connected in a plurality of positions about said third longitudinal axis.

15. The assembly of claim 6, wherein said clamp includes a rod interface washer positioned over a portion of the second bolt, between the first channel and the arm, said rod interface washer being fixed against rotation relative to said bolt.

16. The assembly of claim 15, wherein said arm and said interface washer have mating male protrusions and female cavities on at least a portion of their surfaces such that, when pressed together, the protrusions and cavities facilitate the engagement of said rod interface washer to said arm, preventing rotation of said arm relative to said rod interface washer.

17. The assembly of claim 6, where said mounting portion has a proximal end and said pivot post has a distal end, and the proximal end of said mounting portion and the distal end of said post have mutually engageable male and female contacts, and wherein said contacts are adapted to allow said pivot post to rotate in respect to said mounting portion.

18. The assembly of claim 17, including a snap ring operably connecting said mounting portion and said post.

19. The assembly of claim 17, wherein said clamp includes a rod interface washer positioned over a portion of the second bolt, between the first channel and the arm, said rod interface washer being fixed against rotation relative to said bolt.

20. The assembly of claim 19, wherein said arm and said interface washer have mating male protrusions and female cavities on at least a portion of their surfaces such that, when pressed together, the protrusions and cavities facilitate the engagement of said rod interface washer to said arm, preventing rotation of said arm relative to said rod interface washer.

21. The assembly of claim 20, wherein said arm may be fixedly connected in a plurality of positions about said third longitudinal axis.

* * * * *

UNITED STATES PATENT AND TRADEMARK OFFICE
CERTIFICATE OF CORRECTION

PATENT NO.    : 6,309,391 B1
DATED         : October 30, 2001
INVENTOR(S)   : Crandall et al.

It is certified that error appears in the above-identified patent and that said Letters Patent is hereby corrected as shown below:

<u>Column 6,</u>
Line 54, please remove the comma (,) following the word "being" and insert in lieu thereof -- engaged --.
Line 56, please delete "connector post" and insert in lieu thereof -- pivot post --.
Line 57, please delete "pivot portion" and insert in lieu thereof -- connector portion --.

Signed and Sealed this

Twenty-eighth Day of January, 2003

JAMES E. ROGAN
*Director of the United States Patent and Trademark Office*